United States Patent [19]

Murphy, Jr.

[11] Patent Number: 5,844,997

[45] Date of Patent: Dec. 1, 1998

[54] METHOD AND APPARATUS FOR LOCATING THE ORIGIN OF INTRATHORACIC SOUNDS

[76] Inventor: Raymond L. H. Murphy, Jr., 38 Cypress Rd., Wellesley, Mass. 02181

[21] Appl. No.: 729,272

[22] Filed: Oct. 10, 1996

[51] Int. Cl.$^6$ .................................................. H04R 3/00
[52] U.S. Cl. .............................. 381/92; 381/67; 600/529; 600/528
[58] Field of Search .................. 381/92, 67; 600/508, 600/528, 529; 367/121, 123, 125, 127

[56] References Cited

U.S. PATENT DOCUMENTS

| | | |
|---|---|---|
| 3,990,435 | 11/1976 | Murphy . |
| 4,889,130 | 12/1989 | Lee . |
| 5,010,889 | 4/1991 | Bredesen et al. . |
| 5,165,417 | 11/1992 | Murphy, Jr. . |
| 5,367,506 | 11/1994 | Inanaga et al. ............................ 381/92 |
| 5,465,302 | 11/1995 | Lazzari et al. ............................ 381/92 |
| 5,526,433 | 6/1996 | Zakarauskas .............................. 381/92 |
| 5,627,799 | 5/1997 | Hoshuyama ........................... 381/94.7 |

FOREIGN PATENT DOCUMENTS

| | | |
|---|---|---|
| 4438466A1 | 5/1995 | Germany . |
| 854372 | 8/1981 | U.S.S.R. . |

OTHER PUBLICATIONS

Loudon, R. et al., "State of the Art—Lung Sounds", *Am Rev Respir Dis* 1984: 130:663–673.

Bettencourt, Paul E. et al., "Clinical Utility of Chest Auscultation in Common Pulmonary Diseases", *American Journal of Respiratory and Critical Care Medicine*, Vo. 150, No. 5, Nov. 1994.

Murphy, Raymond L.H. Jr. et al., "Validation of an Automatic Crackle (Rale) Counter", *Am Rev Respir Dis* 1989L 140:1017–1020.

Murphy, Raymond L.H. Jr., "Future Directions and Potentials", *Seminars in Respiratory Medicine*, vol. 6, No. 3, Jan. 1985, pp.: 239–241.

Murphy, Raymond L.H. Jr., "Crackles in the Early Detection of Asbestosis", *Am Rev Respir Dis* 1984, 129:375–379.

*Primary Examiner*—Forester W. Isen
*Attorney, Agent, or Firm*—Cesari and McKenna, LLP

[57] ABSTRACT

A system and method for localizing intrathoracic sounds in a patient. The system utilizes a plurality of microphones placed around the patient. The outputs of the microphones are amplified and filtered by a signal conditioner and converted into digital data streams. The digital data is then analyzed to determine the arrival of a subject at each microphone relative to the arrival time at the first microphone to sense the subject sound. Using equations of motion and the three-dimensional coordinates of the microphones, the system solves for the point of origin of the subject sounds and its speed.

20 Claims, 4 Drawing Sheets

METHOD AND APPARATUS FOR LOCATING THE ORIGIN OF INTRATHORACIC SOUNDS

FIELD OF THE INVENTION

The present invention relates generally to detecting and examining sounds within the human body and, more specifically, to a method and apparatus for localizing the origin of intrathoracic sounds.

BACKGROUND OF THE INVENTION

Since the time of its invention in the early 1800's, the stethoscope has been used routinely by physicians to amplify sounds in the human body. The physician typically places the chest piece of the stethoscope against the patient's skin and listens through the stethoscope's earpieces. By monitoring a patient's breathing, a physician is often able to determine the existence of adventitious (i.e., abnormal and/or unexpected) lung sounds. The identification and classification of adventitious lung sounds, moreover, often provides substantial information about pulmonary and associated abnormalities that are not readily detected by other means, such as roentgenographic (i.e., X-ray) examinations. In addition to analyzing lung sounds, stethoscopes are also frequently used to monitor the functioning of other internal organs such as the heart.

As a device to locate the origin of an intrathoracic sound, the stethoscope provides only limited information. For example, a physician may be able to determine the approximate location of a lung infection. The physician will not, however, be able to identify the precise point of origin of an adventitious sound. In addition, the amount of information that can be obtained from a stethoscope depends significantly on the skill and experience of the physician or other person using the stethoscope. Even skilled physicians often disagree as to the classification and location of certain pulmonary sounds.

Accordingly, efforts have been made to develop devices that can determine the origin of intrathoracic sounds with greater precision than the conventional, monaural stethoscope. For example, stethoscopes having two chest pieces, known as binaural stethoscopes, provide some improvement in localizing lung sounds. In addition, as described in S. Kraman *Determination of the Site of Production of Respiratory Sounds by Subtraction Phonopneumography* Am Rev Respir Dis 1980; 122:303, Kraman utilized two microphones applied to the chest wall a few centimeters apart in an effort to locate the origin of certain sounds. Kraman then derived a "subtraction intensity index" based on the idea that the sound waves recorded at the two microphones should be relatively similar if the sound was produced at a single, distant source and dissimilar if the sound was produced locally by different sources. Applying his subtraction intensity index, Kraman concluded that the inspiratory phase of vesicular sound is produced in the lung somewhere in-between the upper airways and the alveoli. Kraman further concluded that the expiratory phase of vesicular sound is produced more centrally than the inspiratory phase.

Efforts have also been directed toward the recording of lung sounds in order to discern additional information of the sound through subsequent analysis. For example, U.S. Pat. No. 3,990,435, entitled BREATH SOUND DIAGNOSTIC APPARATUS to Murphy, the applicant herein, discloses a system for providing a time-expanded visual record of breath sounds to improve the detection of breathing abnormalities, such as rhonchi. In addition, U.S. Pat. No. 5,010,889, entitled INTELLIGENT STETHOSCOPE to Bredesen et al., discloses a stethoscope capable of digitizing and storing body sounds. These sounds are then categorized and compared to sound representations of particular abnormalities that are stored within an information storage/retrieval system. If a match is found, the stethoscope displays the diagnosis to the physician on a graphics panel.

The ability to locate the point of origin of certain body sounds may provide significant advantages in the diagnosis and treatment of disease. Knowing the precise origin of abnormal sounds and the surrounding anatomy, for example, may lead to a better understanding as to the mechanism for generating the abnormal sound and, hence, its likely cause(s). In addition, the localization of intrathoracic sounds may be used to confirm results obtained via other diagnostic tools, such as CT scans, without exposing the patient to the risks associated with invasive diagnostic procedures. Furthermore, knowledge as to the source of normal body sounds aids in the understanding of sound production within the human body. The prior art methods or systems, however, are unable to determine the point of origin of intrathoracic sounds with sufficient precision to provide more than minimal assistance in the diagnosis or study of disease.

SUMMARY OF THE INVENTION

It is an object of the present invention to provide a system capable of determining the origin of body sounds, primarily intrathoracic sounds.

It is a further object of the present invention to provide a system capable of determining the speed of body sounds.

It is a further object of the present invention to provide a noninvasive technique for diagnosing disease.

It is a still further object of the present invention to provide a diagnostic tool that may be used to correlate the results obtained from other diagnostic procedures.

Briefly, the invention utilizes a plurality of microphones preferably attached about the chest area of a patient. The three-dimensional coordinates of each microphone are then measured relative to a given datum point. As the patient breathes, the microphones translate the sounds generated within the patient's chest cavity into audio signals. These signals, which are preferably amplified and filtered, are then transformed by analog-to-digital converters into a digital data stream. The audio information from all of the microphones is then analyzed to identify a subject sound, typically adventitious, and to determine the sound's arrival time at each microphone. The arrival times are preferably measured relative to the time at which the first microphone picked-up the subject sound. Using equations of motion and the geometric relationships between the sound source and the microphones, a computer processor preferably solves for the point of origin of the sound and its speed. These results may be displayed graphically in relation to anatomic features on a graphical user interface and/or printed.

In the illustrated embodiment, the digitized audio signals from each microphone are paired with a master clock signal and stored in a computer memory for subsequent access by a processor. The audio information generated by each microphone is then preferably displayed simultaneously on the graphical user interface as a waveform, preferably in a time-expanded format. An operator then identifies the subject sound, locates its beginning point as recorded by each microphone and determines the corresponding arrival time at each microphone (relative to the arrival time at the first microphone to pick-up the sound). That is, relying on the master clock signal paired with each audio signal, the operator determines the delta time taken for the subject sound to be picked-up at each of the remaining microphones after the first microphone sensed the sound.

Next, the operator may enter the three-dimensional coordinates of each microphone and the corresponding arrival time of the subject sound into the system preferably using a computer input device, such as a keyboard or mouse. The operator may also assume an initial speed for the subject sound and enter this information as well. The computer processor then preferably utilizes an iterative process based on equations of motion to determine the actual speed of the subject sound and its point of origin within the patient's body.

BRIEF DESCRIPTION OF THE DRAWINGS

The above and further advantages of the invention may be better understood by referring to the following description in conjunction with the accompanying drawings, in which.

DESCRIPTION OF THE PREFERRED EMBODIMENT

Figure 1:
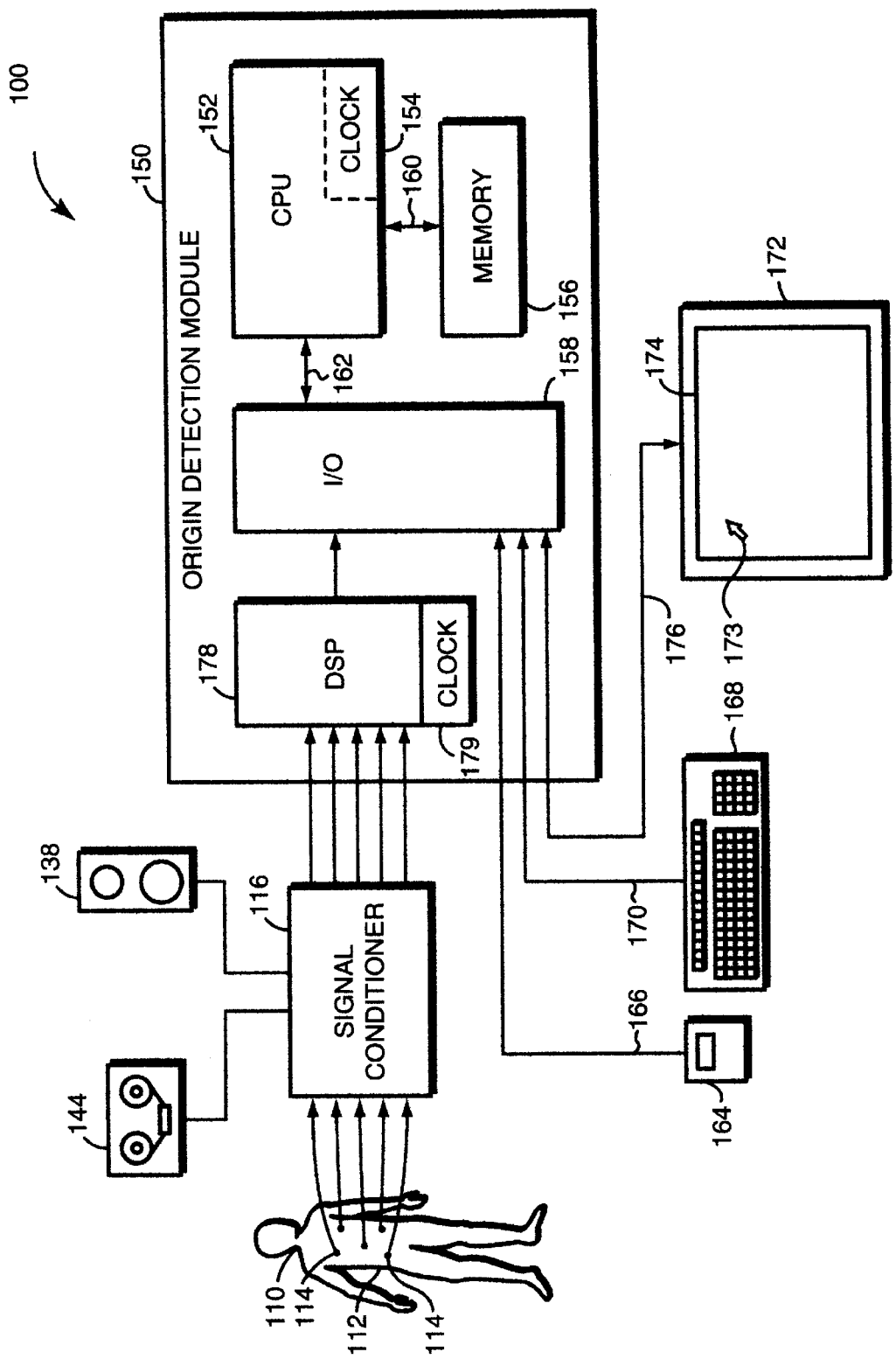
FIG. 1 is a highly schematic illustration of the system of the present invention.

FIG. 1 illustrates a system 100 for locating the origin of intrathoracic sounds of a patient 110 having a chest area 112. The system 100 utilizes a plurality of microphones 114 that are attached to the patient 110 preferably around the chest area 112. For example, the microphones 114 may be attached to the patient's right hemithorax in superior, anterior, posterior and lateral locations. To provide some degree of isolation from external sounds, the microphones 114 may be embedded in the chest pieces of conventional stethoscopes (not shown). In addition, the microphones 114 are preferably taped to the patient 110 to prevent dislocation during operation of the system 100.

The microphones 114 sense intrathoracic sounds from the patient 110 and translate those sounds into audio signals (not shown). Lung sounds may be sensed during quiet breathing, forced expiration and/or during suctioning through a bronchoscope. The audio signals which are output from each microphone 114 are initially provided to a signal conditioner 116.

Figure 2:
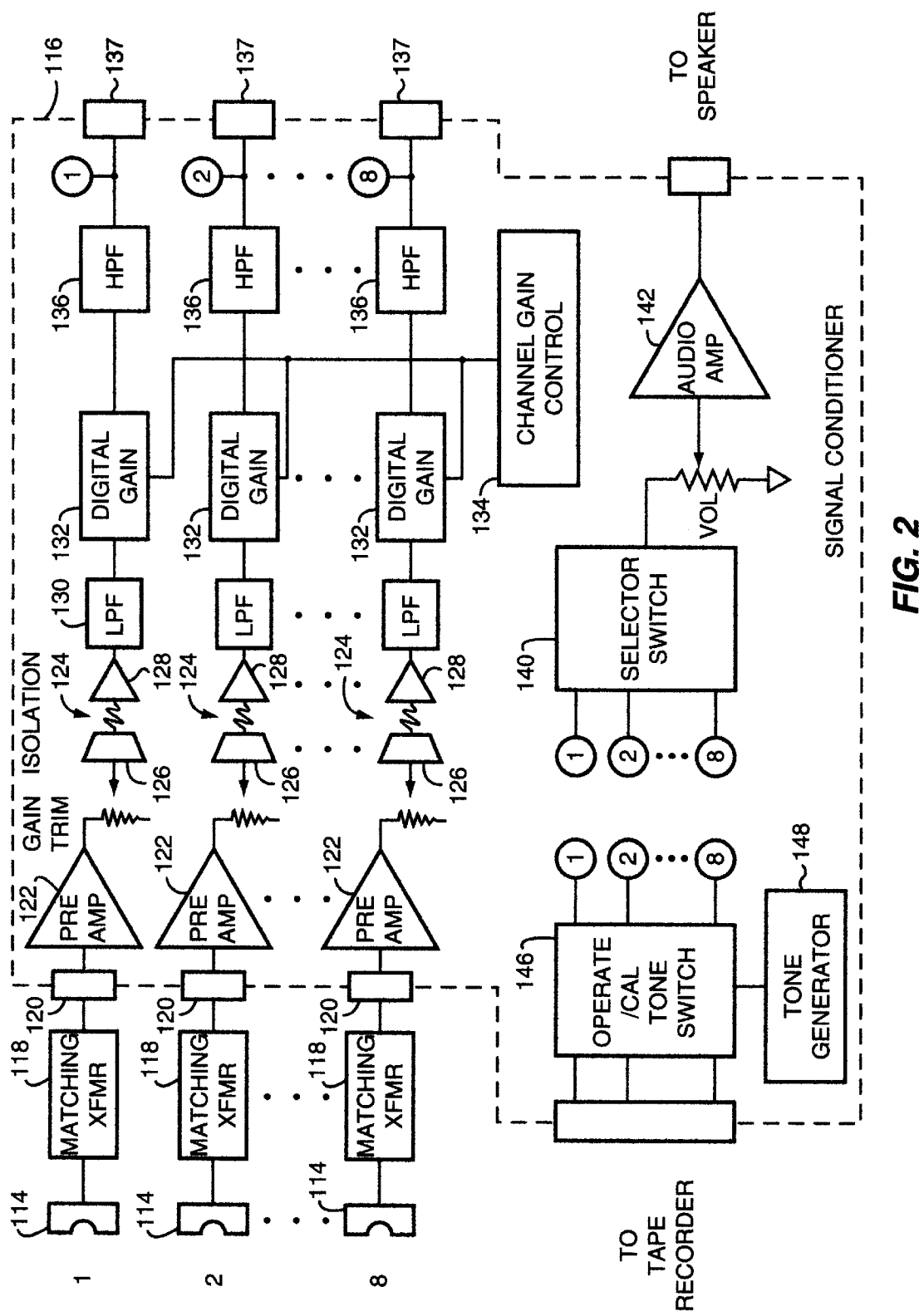
FIG. 2 is a highly schematic illustration of the signal conditioner of the system of FIG. 1.

Referring to FIG. 2, each microphone 114 may include a corresponding transformer 118 for matching the impedance of the microphone 114 with the signal conditioner 116 and thus preserving the typically weak audio signal for subsequent processing. The matched audio signals from each microphone 114 are then connected to a separate input channel 120 of the signal conditioner 116. In general, the signal conditioner 116 modifies the audio signals in order to remove unwanted noise and boost the signal strength for subsequent processing.

First, the audio signals from each microphone 114 are amplified by a preamp 122. The preamps 122 preferably provide a unity gain to the signal. Next, the signals are preferably passed through an isolation device 124 to ensure patient safety. That is, should an electrical failure occur somewhere in the system 100 (FIG. 1), the isolation devices 124 prevent any voltage from reaching the microphones 114 and possibly injuring the patient 110. For example, each isolation device 124 may be an opto-isolator comprising a phototransmitter 126 that translates the audio signal output from the preamp 122 into a corresponding optical signal that is then received by a photoreceiver 128 and converted back to an electrical signal. Since the phototransmitter 126 can only convert an electrical signal into an optical signal and since the photoreceiver 128 can only convert the optical signal into an electrical signal, the isolation device 124 prevents any voltage from reaching the patient 110 (FIG. 1).

From the isolation devices 124, the audio signals may be filtered through a low pass filter 130 preferably having a cut-off frequency on the order of 2000 Hz. The filtered audio signals are then amplified by a digital gain device 132. A channel gain control 134, which may be adjusted by the operator of the system 100 (FIG. 1), preferably sets the amount of gain equally at all channels 120. The gain is preferably adjustable by the control 134 in roughly logarithmic steps from 1 to 100, e.g., 1, 1.25, 2, 5, 10, 20, 50 and 100. Since the digital gain device 132 may introduce unwanted noise into the audio signals, each channel is then fed through a high pass filter 136. The high pass filters 136 preferably have a cut-off frequency on the order of 80 Hz. The filters 130, 136 thus encompass the frequency range of interest, namely 80 to 2000.

The low and high pass filters 130, 136 may be conventional second-order Butterworth filters. Alternatively, the low and high pass filters may be replaced with band-pass filters preferably having a band pass of 80 to 2000 Hz.

The audio signals from each microphone 114 are now sufficiently conditioned for subsequent processing and analysis. The signal conditioner 116, moreover, preferably includes an output channel 137 corresponding to each microphone 114 so that the signals may be provided to other components of the system 100 as described below. The processed audio signals also may be selectively provided to a speaker 138 (FIG. 1) for playback to the operator. Specifically, the audio signals may be provided to a selector switch 140 and an adjustable audio amplifier 142 that is capable of driving the speaker 138 or, alternatively, a pair of earphones (not shown). The selector switch 140 allows the operator to select which channel 137 is connected to the speaker 138 for play-back. The amplifier 142, moreover, preferably allows the operator to adjust the volume during play-back. Thus, the operator may monitor the audio information from a selected microphone 114. Accordingly, if the operator observes some external noise being picked-up by the microphone 114, the operator may decide to re-start the test.

The processed audio signals may also be transmitted to a tape recorder 144 (FIG. 1) for storage. In particular, the signals, after passing through the high pass filters 136, are fed to an operate/calibrate tone switch 146. In the calibrate mode, the switch 146 blocks all audio signals from the microphones 114 and passes a tone produced by a tone generator 148 to the recorder 144. The tone is preferably used to set the recording levels of the recorder 144 to appropriate values prior to a recording session. Once the levels on the recorder 144 are properly set, the switch 146 is moved to the operate mode, thereby connecting the processed audio signals from all of the microphones 114 to the recorder 144 and blocking the tone generator 148. The audio signals may then be recorded on the tape recorder 144.

The tape recorder 144 may be any high fidelity magnetic tape recorder, such as a reel-to-reel recorder or cassette recorder.

Referring back to FIG. 1, the outputs from the signal conditioner 116 (i.e., the processed audio signals from each microphone 114) are preferably provided to an origin detection module 150. The origin detection module 150, which may be implemented, in part, using a personal computer, includes a central processing unit (CPU) 152. The CPU 152 is coupled to a memory 156 and input/output circuitry 158 by bi-directional buses 160 and 162. The memory 156 typically comprises random access memory (RAM) (not shown) for the temporary storage of information, including application programs (not shown) and an operating system (not shown) and read only memory (ROM) (not shown) for permanent storage of the computer's configuration and basic operating commands. The operating system controls the operations of the CPU 152.

The I/O circuitry 158 preferably connects the origin detection module 150 to cursor/pointer control and input devices, such as a mouse 164 (via cable 166) and a keyboard 168 (via cable 170). A graphical user interface 172 having a display screen 174 is also preferably connected to the I/O circuitry 158 via cable 176. A pointer or cursor 173 may be displayed on the screen 174 and its position may be controlled via the mouse 164 or the keyboard 168 in a conventional manner. The input/output circuitry 158 preferably contains the necessary hardware, e.g., buffers and adapters, needed to interface with the control devices 164, 168, the graphical user interface 172 and the memory 156.

The origin detection module 150 is preferably a personal computer of the IBM® series of computers sold by International Business Machines® or the Macintosh® series of computers sold by Apple Computer Inc. These computers have resident thereon, and are controlled and coordinated by, operating system software, such as IBM OS2®, Microsoft® Windows 95® or Apple® System 7® operating systems. It should be understood that the system 100 may also be implemented on other computer platforms, such as UNIX-based workstations manufactured and sold by Hewlett Packard.

As mentioned above, the signal conditioner 116 is preferably connected to the origin detection module 150 such that the processed audio signals from each microphone 114 are received by the origin detection module 150. Specifically, each output channel 137 from the signal conditioner 116 is connected to a digital signal processor 178 that may be part of the origin detection module 150. The digital signal processor 178 preferably includes an analog-to-digital converter (not shown) for converting the processed analog audio information into a digital data stream. The digital signal processor 178 may have a separate analog-to-digital converter for each microphone 114. The sampling rate of the digital-to-analog converters are preferably on the order of 8000 samples per second and the bit rate is preferably 8 bits per sample.

The digital signal processor 178 preferably includes a system clock 179 for providing a master time signal that may be synchronously paired with the digital audio information corresponding to each microphone 114. That is, the master time signal is simultaneously paired with all of the digital audio signals to provide a single, uniform time reference to the signals received from each microphone 114. The paired digital audio/time information associated with each microphone 114 is then forwarded from the digital signal processor 178 to the input/output circuitry 158, where it is preferably transferred by the CPU 152 to a portion of memory 156 for storage.

The digital signal processor 178 is preferably a data acquisition printed circuit board, such as those manufactured and sold by Keithley Metrabyte, Inc. It should be understood that the master clock signal, rather than being provided by the digital signal processor 178, may be provided from a system clock 154 internal to the CPU 152.

At the request of the operator, the stored audio/time information corresponding to each microphone 114 may be retrieved by the CPU 152 and visually displayed, preferably as a waveform, on the graphical user interface 172. As discussed in U.S. Pat. No. 3,990,435, the entirety of which is hereby incorporated by reference, the visual representation of the audio/time information associated with each microphone 114 is preferably displayed on an expanded scale of 800 millimeters per second or higher. At this expanded scale, various breathing abnormalities, such as rales and rhonchi, are readily detected and easily differentiated. Preferably, the master time information is also displayed along with the visual representation of the audio information corresponding to each microphone 114. By reviewing the displayed audio information, the operator can easily locate the beginning of the subject sound as recorded by each microphone 114. Furthermore, by comparing the various times at which each microphone 114 first sensed the subject sound, the operator can determine its arrival time relative to the arrival time at the first microphone to record the subject sound.

Figure 3:
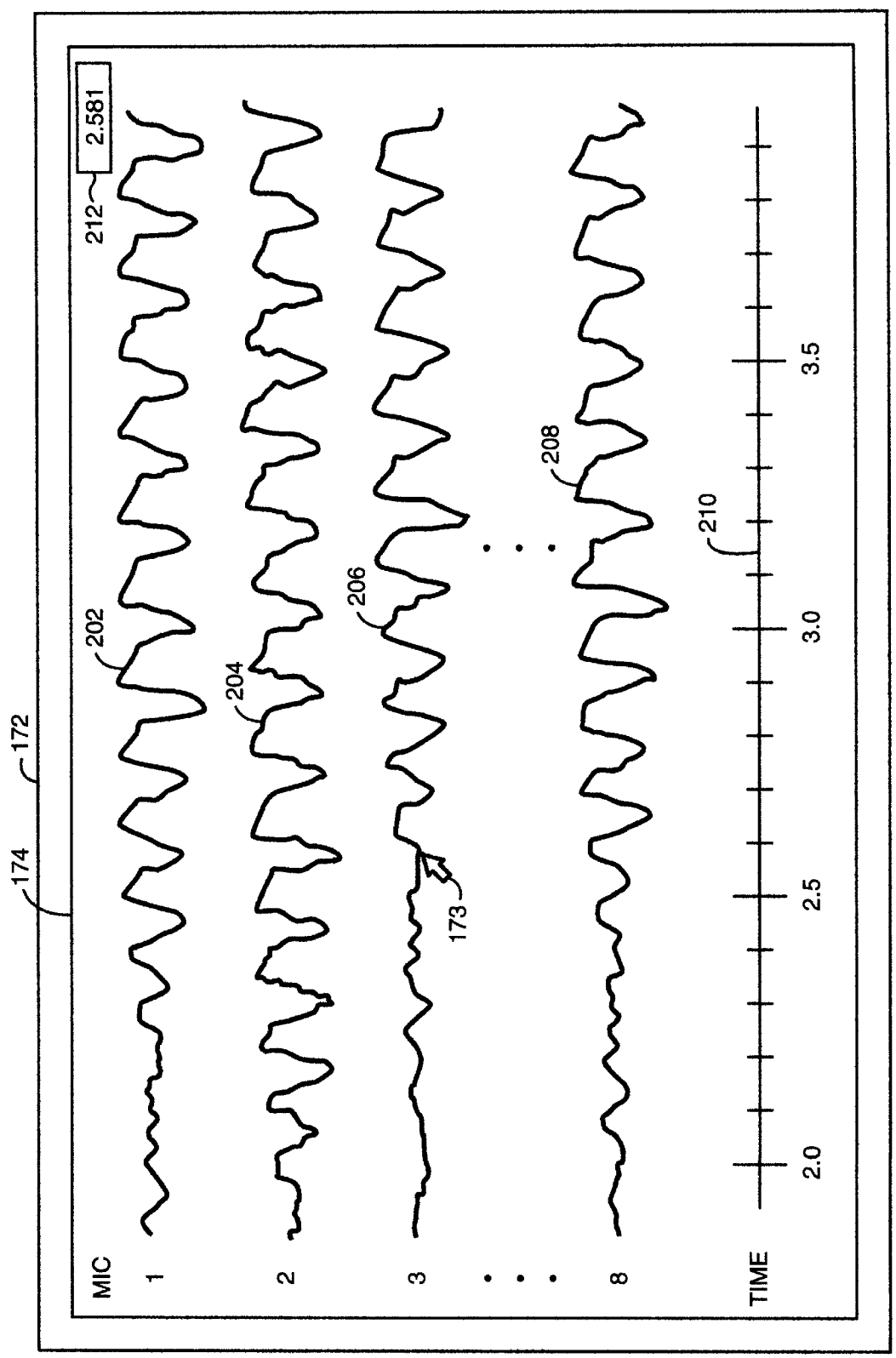
FIG. 3 is an illustration of the display screen of FIG. 1 showing pre-recorded audio information.

In the illustrated embodiment, an application program (not shown) running on the origin detection module 150 is used to visually display the audio/time information stored in the memory 156. As shown in FIG. 3, the audio information recorded by each microphone 114 (FIG. 1) is preferably displayed as an expanded waveform on the display screen 174 of the graphical user interface 172. More specifically, the audio information recorded by microphone number one is represented by the waveform labeled 202, the information recorded by microphone number two is labeled 204, the information recorded by microphone number three is labeled 206 and so on to the information recorded by the last microphone (e.g., number 8) which is labeled 208. A time line 210 corresponding to the paired master clock signal is also displayed.

The application program, moreover, preferably slaves the pointer 173 displayed on the display screen 174 to the master time signal, as shown by the time line 210. That is, as the operator moves the pointer 173 across the screen 174 with the mouse 164 (FIG. 1), a read-out 212 of the master time corresponding to the pointer's position on the display screen 174 is shown. Accordingly, the operator need only place the pointer 173 at the point along the visual representation of the audio information corresponding to the beginning of the subject sound in order to determine the time at which the sound reached that microphone. For example, as shown in FIG. 3, by placing the pointer 173 at the beginning of the subject sound as recorded by microphone number three, the read-out 212 displays the corresponding time, namely 2.581 seconds. By repeating this process for the waveforms corresponding to each microphone and comparing these times, the operator may obtain the arrival times of the subject sound at each microphone 114 relative to the time at which the first microphone sensed the subject sound. As shown in FIG. 3, microphone number two is the first microphone to sense the subject sound.

Based on the functional description above, one skilled in the art would be able to develop an application program to manipulate the stored audio data in order to perform these steps. The application program, moreover, may be written in a conventional programming language, such as C. It should be understood that the application program may be written so that the arrival times are determined by the computer rather than the operator.

It should be further understood that the audio information sensed by the microphones alternatively may be provided to a strip chart modified to present the waveform in a time-expanded format. By reviewing the strip charts, the operator may determine the arrival time differences of a subject sound. Most strip charts in use today, however, are too imprecise to provide the level of detail that is required.

Once the operator has determined the arrival times of the subject sound at each microphone 114 (relative to the first microphone to record the sound) the operator preferably executes another application program for determining the point of origin of the subject sound and its speed. This second application program (not shown) may run on the origin detection module 150 (FIG. 1) or it may run on a separate computer. In the preferred embodiment, the second application program prompts the operator for the three-dimensional coordinates of each microphone and the corresponding arrival time of the subject sound at that microphone. The second program also prompts the operator for an initial sound speed from the operator.

The three-dimensional coordinates of the microphones may be determined by measuring the locations of the microphones by hand using a ruler and a carpenter's square relative to a datum point, such as the patient's sternum. The three-dimensional coordinates of the microphones may also be determined by using a photographic enlargement stand having carpenter squares attached thereto. In this case, the microphones are attached to the patient and the patient is photographed standing behind the enlargement stand. The operator may then determine the coordinates of the microphones by reviewing the photograph(s). This procedure also preserves a record of the locations of the microphones. It should be understood that commercially available electronic locator devices may be utilized with the system 100 (FIG. 1) in order to determine their 3-dimensional coordinates.

The second application program implements a set of equations of motion, described below, for the subject sound and solves for the three-dimensional coordinates for the origin of the sound and its speed. The application program may be written in any conventional computer programming language, such as C or Matlab, which are well known to those skilled in the art.

We now proceed to develop the equations of motion for determining the origin of the subject sound. Let $t_i$ be the time taken for the sound to travel from its source to the $i^{th}$ microphone, having coordinates: $x_i$, $y_i$, $z_i$. Assuming the sound velocity, v, is isotropic, then the coordinates of the sound source must lie on the surface of a sphere of radius $R_i = vt_i$ about the $i^{th}$ microphone. Applying the equation for a sphere, we have:

$$(x-x_i)^2+(y-y_i)^2+(z-z_i)^2=v^2t_i^2=R_i^2 \qquad (1)$$

where x, y and z are the coordinates of the sound source. Since we have a plurality of microphones and the sound source must lie on the surface of a sphere about each microphone, the coordinates x, y and z correspond to the point of intersection of the spheres associated with the microphones.

Nonetheless, we do not know at what time the sound began, thus, we do not know the time $t_i$. Instead, as set forth above, we have measured the arrival time of the sound at each microphone relative to the first microphone to sense the sound. Assume that the $k^{th}$ microphone having coordinates $x_k$, $y_k$ and $z_k$ is the first to sense the sound and the time taken for the sound to travel from the source to this microphone is $t_k$. We may then write the time taken for the sound to reach the other microphones in terms of $t_k$. That is, assuming the measured arrival time at the $i^{th}$ microphone, relative to the $k^{th}$ microphone, is $\tau_i$, then $t_i = \tau_i + t_k$. Moreover, $R_i = vt_i = v(\tau_i + t_k) = V\tau_i + vt_k = V\tau_i + R_k$, so that equation (1) now becomes:

$$(x-x_i)^2+(y-y_i)^2+(z-z_i)^2=v^2t_i^2=(v\tau_i+R_k)^2 \qquad (2)$$

where $$R_k = \sqrt{(x-x_k)^2+(y-y_k)^2+(z-z_k)^2}$$

Accordingly, one possible approach would be to measure the arrival times at a minimum of five microphones, thereby obtaining four arrival time values. These values may then be substituted into four sets of equation (2) and solved for the four unknowns: x, y, z and v. This approach, however, which involves non-linear equations for the unknown parameters is quite cumbersome and would require substantial processor power.

As an alternative, consider that the intersection of two spheres (that intersect at more than one point) is a circle and that a circle lies in a single plane. We deliberately choose to develop the solution for the sound source through the intersection of planes, rather than circles, because the equation for a plane (as shown below) is linear in the coordinates of the sound source (x, y, z).

The equation for the plane defining the intersection of two spheres (i and j) may be found by subtracting the two equations for the spheres (e.g., equation (1)) and is given by:

$$a_{ij}x+b_{ij}y+c_{ij}z=d_{ij} \qquad (3)$$

where $$\begin{bmatrix} a_{ij} \\ b_{ij} \\ c_{ij} \end{bmatrix} = \begin{bmatrix} x_i - x_j \\ y_i - y_j \\ z_i - z_j \end{bmatrix}$$

and $$d_{ij}=\tfrac{1}{2}[(x_i^2+y_i^2+z_i^2)-(x_j^2+y_j^2+z_j^2)-R_i^2+R_j^2] \qquad (4)$$

where $$R_i = vt_i \text{ and } R_j = vt_j$$

Recall that we can rewrite $R_i$ and $R_j$ in terms of the measured arrival times at those microphones and the radius $R_k$ (which is the distance from the sound source to the first microphone to sense the subject sound). Equation (4) thus becomes:

$$d_{ij}=\tfrac{1}{2}(x_i^2+y_i^2+z_i^2)-\tfrac{1}{2}(x_j^2+y_j^2+z_j^2)+\tfrac{1}{2}(\tau_j^2-\tau_i^2)v^2+(\tau_i-\tau_j)vR_k$$

Specifically, the intersection of planes corresponding to microphone numbers 1 and 2, numbers 1 and 3 and numbers 1 and 4 may be written as follows:

$$a_{12}x+b_{12}y+c_{12}z=d_{12}$$

$$a_{13}x+b_{13}y+c_{13}z=d_{13}$$

$$a_{14}x+b_{14}y+c_{14}z=d_{14}$$

which we denote as (1, 2), (1, 3) and (1, 4), respectively, for brevity. Moreover, the intersection of planes (1, 2) and (1, 3) may be solved simultaneously to determine the line of intersection of the two planes. Similarly, the intersection of planes (1, 2) and (1, 4) may be solved simultaneously to determine the line of intersection of these two planes. The point at which these two lines intersect is the sound source.

The fact that all of the equations for the planes contain terms that are quadratic in v but linear in R, determines the order in which the unknown parameters may be eliminated in the solution. That is, we first determine $R_k$ in terms of v by assuming an initial value for v. We then determine the actual value of v by a numerical iterative method, since it occurs as a non-linear parameter.

Figure 4:
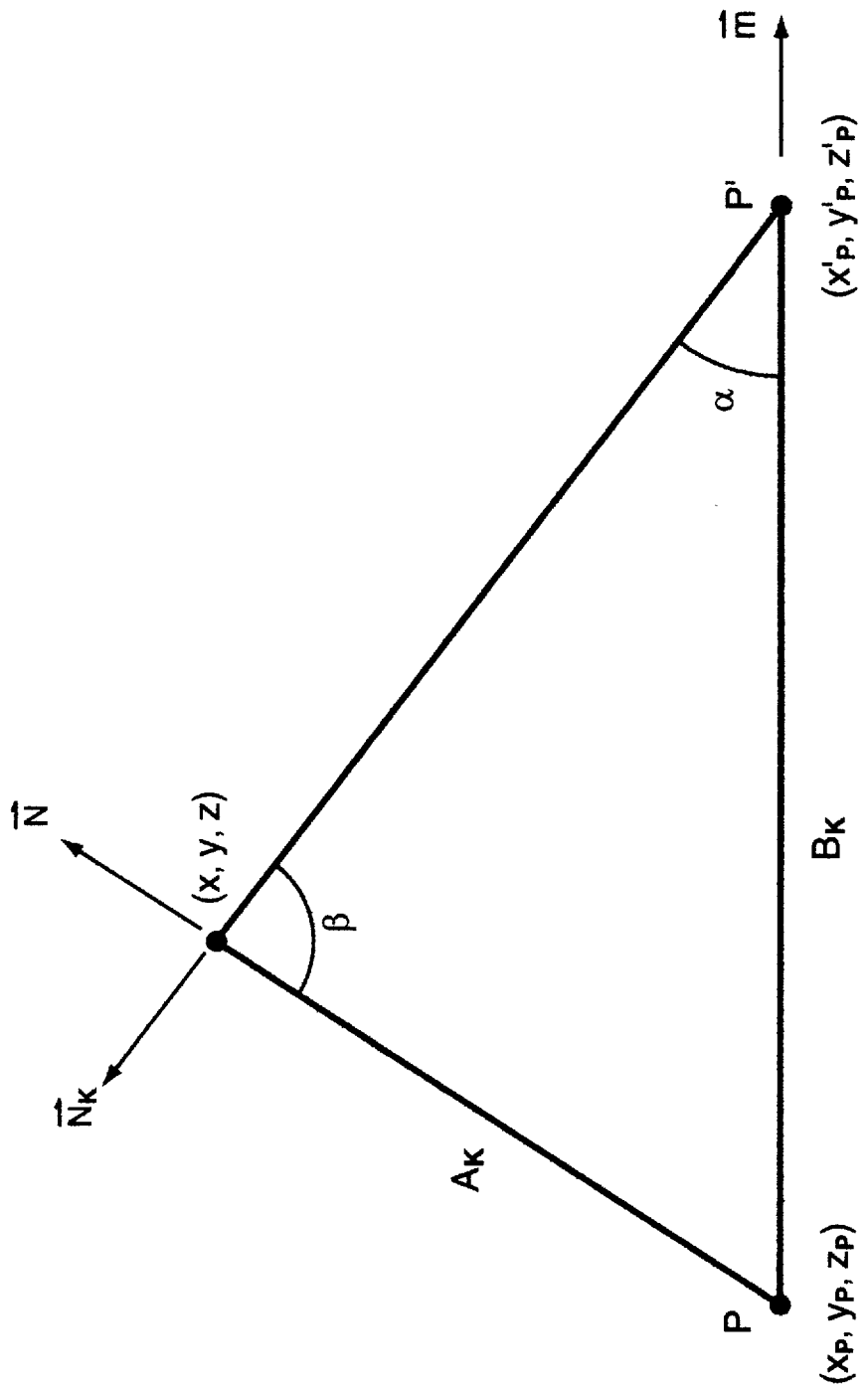
FIG. 4 illustrates the geometry of a preferred solution implemented by the present invention.

Referring now to FIG. 4, the location of the sound source, having coordinates (x, y, z), may be considered as the intersection of two vectors $\vec{N}$ and $\vec{N}_k$ in the (1, 2) plane defined above. The line of intersection of planes (1, 2) and (1, 3) is specified by the direction of unit vector $\vec{N}$ and a point on the line, designated P, having coordinates ($x_p$, $y_p$, $z_p$). Assuming P lies in the x-y plane for convenience, then $z_p$=0. Similarly, the line of intersection of the planes (1, 2) and (1, k), where k=4 or 5 (i.e., we repeat the above planar solution substituting microphone 4 for microphone 5 to obtain another expression of the sound source) is specified by the unit vector $\vec{N}_k$ and the point P', which is also chosen to lie in the x-y plane for convenience. The vector M is given by $$\vec{M} = \frac{b_{12}\vec{i} - a_{12}\vec{j}}{\{a^2_{12} + b^2_{12}\}^{1/2}}$$

and the vectors $\vec{N}$ and $\vec{N}_k$ are $$\vec{N} = \pm \frac{\vec{N}_{12} \times \vec{N}_{13}}{|\vec{N}_{12} \times \vec{N}_{13}|} \quad (5)$$

$$\vec{N}_k = \pm \frac{\vec{N}_{12} \times \vec{N}_{1k}}{|\vec{N}_{12} \times \vec{N}_{1k}|}, k = 4, 5 \quad (6)$$

where $\vec{N}_{ij} = a_{ij}\vec{i} + b_{ij}\vec{j} + c_{ij}\vec{k}$

In the above, we have used $\vec{i}$, $\vec{j}$, $\vec{k}$ for unit vectors along the x,y,z axes, respectively, and standard notations for the vector cross products and absolute magnitudes. The algebraic signs in equations (5) and (6) are preferably chosen such that the z-components are negative. This choice follows from the convention preferably used for the location of the microphone coordinates. That is, the x-y plane is tangent to the front of the patient's chest and the z-axis is pointed outward. Consequently, the negative z-components for the vectors $\vec{N}$ and $\vec{N}_k$ simply means that we are looking for a sound source inside the chest.

The angles in FIG. 4 may be given by $\sin\alpha = |\vec{M} \times \vec{N}_k|;$ $\sin\beta = |\vec{N} \times \vec{N}_k|$ and we use the law of sines to write, $$A_k = B_k \frac{\sin\alpha}{\sin\beta} \quad (7)$$

Once numerical values of $A_k$ are obtained, then the coordinates of the source are given by $x = x_p + N_x A_k \quad (8)$ $y = y_p + N_y A_k \quad (9)$ $z = N_z A_k \quad (10)$ The unknown parameters v and R are contained in $x_p$, $y_p$ and $A_k$ through its dependence on $B_k$ where $B_k = [(x'_p - x_p)^2 + (y'_p - y_p)^2]^{1/2} \quad (11)$ where $x_p$, $y_p$ and $x'_p$, $y'_p$ are solutions of $$\begin{pmatrix} a_{12}x_p + b_{12}y_p = d_{12} \\ a_{13}x_p + b_{13}y_p = d_{13} \end{pmatrix} \text{ and } \begin{pmatrix} a_{12}x'_p + b_{12}y'_p = d_{12} \\ a_{1k}x'_p + b_{1k}y'_p = d_{1k} \end{pmatrix} k = 4, 5$$

As described above, we first assume an initial value for v, say 5 to 10 centimeters/second, and solve for R. We note that since the $d_{ij}$'s are linear in R, so will be $x_p$, $y_p$, $x'_p$ and $y'_p$; but $B_k$ as written in equation (11) is not. Accordingly we use geometric relationships to write $$B_k = |x'_p - x_p| \left\{ 1 + \left(\frac{a_{12}}{b_{12}}\right)^2 \right\}^{1/2} \text{ for } b_{12} \neq 0 \quad (13)$$

In the event $b_{12}=0$, then we use $B_k = |y_p - y'_p| \quad (14)$

Equations (13) and (14) are linear in R, but the procedure for taking the absolute magnitude is not clear. To illustrate the difficulty, note that the quantity $c_1 - c_2 R$, with positive values of $c_1$ and $c_2$, can either be positive or negative depending on the value of R. The resolution of this difficulty is to simply ignore the absolute magnitude signs in equations (13) and (14) and use equation (7) to obtain expressions for $A_k$ with k=4, 5. We then determine R from $A_4 = \pm A_5$ (i.e., first assume $A_5$ is positive and then assume $A_5$ is negative). This produces two numerical values for R, and the correct one is chosen by physical arguments. For example, R must be positive and limited in magnitude by the size of the human chest.

At this point, we have assumed a trial value for v and solved for R. This value of R is inserted in equations (7–9) to get initial values of (x,y,z). This solution for x, y and z is then used to calculate arrival time differences to compare with the measured arrival time differences, and a new value of v may be found by a least squares analyses. That is, we look for a new velocity $v' = v + \Delta v$ such that $$\sum_{i=1}^{5} (\tau_i - \tau_i')^2 \text{ is minimized.}$$

In this expression, $\tau_j'$ is the calculated arrival time difference, $$\tau_i' = \frac{[(x_i - x)^2 + (y_i - y)^2 + (\tau_i - \tau)^2]^{1/2} - R}{v} \quad (15)$$

which is calculated using the initial value for v. The solution for $\Delta v$ is $$\Delta v = \left[ \sum_{i=1}^{5} (\tau_i - \tau_i') \frac{\partial \tau_i'}{\partial v} \right] \cdot \sum_{i=1}^{5} \left( \frac{\partial \tau_i'}{\partial v} \right)^2 \right]^{-1} \quad (16)$$

Here, the partial derivatives are calculated numerically, and the processes are repeated for convergence. In practice, no more than three iterations have been required to obtain the location of the sound source and its velocity within the degree of accuracy of the arrival time measurements.

Results for a particular example are tabulated below. Measured microphone locations and arrival time data are listed in Table A1 below. Starting with an assumed value of v=9.0 cm/ms, the calculated values of the parameters are shown in Table A2 for two subsequent iterations. Calculated values of the arrival times after each iteration are shown in Table A3. It should be noted that the values listed in the last row of Table A3, which were calculated with the parameters v, x, y, z in the last row of Table A2, are indistinguishable from the measured values listed in the last row Table A1. This demonstrates that the values for x, y, z and v obtained by this method uniquely reproduces the measured arrival time differences.

TABLE A1

Microphone Coordinates and Arrival Time Data

| Microphone i = 1, ... 5 | 1 | 2 | 3 | 4 | 5 |
|---|---|---|---|---|---|
| $x_i$ (cm) | −12.4 | −12.4 | −15.2 | −15.8 | −6.9 |
| $y_i$ (cm) | 7.0 | −0.8 | −8.7 | −9.3 | −5.6 |
| $z_i$ (cm) | −8.3 | 0.0 | 0.0 | −8.3 | −21.6 |
| $\tau_i$ (ms) | 0.056 | 0.0 | 0.378 | 0.168 | 0.887 |

TABLE A2

Iterative Solution for Parameters x,y,z and v
Starting with v = 9.0 cm/ms
Calculated Parameters

| Iteration | v (cm/ms) | R (cm) | x (cm) | y (cm) | z (cm) | Δv (cm/ms) | v' (cm/ms) |
|---|---|---|---|---|---|---|---|
| — | 9.0 | 8.3541 | −12.3349 | −.9392 | −7.4233 | 0.6047 | 9.6047 |
| 1 | 9.6047 | 7.5083 | −12.5598 | −.9048 | −7.4095 | 0.0742 | 9.6789 |
| 2 | 9.6789 | 7.4103 | −12.5885 | −.9004 | −7.4078 | | |

TABLE A3

Calculated Arrival Time Differences $\tau_i'$ (milliseconds)

| Iteration | v (cm/ms) | $\tau_1'$ | $\tau_2'$ | $\tau_3'$ | $\tau_4'$ | $\tau_5'$ |
|---|---|---|---|---|---|---|
| — | 9.0 | −.0407 | −.1032 | 0.3068 | 0.0821 | 0.8364 |
| 1 | 9.6047 | 0.0467 | −.0103 | 0.3713 | 0.1598 | 0.8823 |
| 2 | 9.6789 | 0.0561 | 0.0001 | 0.3780 | 0.1680 | 0.8870 |

It should be understood that if the number of measured arrival times exceeds the number of parameters to be determined, then the distribution of possible solutions can be investigated. That is, depending on which arrival times are used in the above solution, slight variations in the sound source location and velocity will occur. These variations may be analyzed in a straight-forward way using standard matrix techniques to obtain a non-linear, least-squares fit to the data. The results, moreover, may be expressed in terms of mean values for x, y, τ and v as well as their standard deviations.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A system for localizing intrathoracic sounds utilizing a plurality of microphones attached to a subject, each microphone having a set of three-dimensional coordinates and providing an audio output, the system comprising:

A. a signal conditioner connected to the plurality of microphones, the signal conditioner processing the audio outputs of the microphones to remove unwanted noise and boost signal strength;

B. digitizing means connected to the signal conditioner for converting the processed and modified audio outputs for each microphone into a corresponding digital data stream; and C. an origin detection module connected to the digitizing means for receiving the digital data streams, the origin detection module having a display screen, wherein the origin detection module is capable of displaying the digital data stream for each microphone in a time-expanded format on the display screen, such that an arrival time for the intrathoracic sounds may be determined at each microphone, and determining the three dimensional location of the intrathoracic sounds based upon the set of three-dimensional coordinates and the arrival time for each microphone.

2. The system of claim 1 wherein the digitizing means comprises at least one analog-to-digital converter for converting the audio outputs into the digital data streams and a clock for outputting a master time signal such that the digitizing means synchronously pairs the master time signal with the digital data stream for each microphone.

3. The system of claim 2 wherein the origin detection module displays the synchronous time signal along with the digital data stream for each microphone so that the arrival times may be determined.

4. The system of claim 3 wherein the origin detection module further comprises an input device and a pointer for display on the display screen, such that movement of the pointer across the display screen is controlled by the input device.

5. The system of claim 4 wherein the pointer has a position on the display screen and the pointer is slaved with the master time signal so that a time read-out, corresponding to the position of the pointer on the display screen, is provided on the display screen thus permitting the arrival times to be determining by positioning the pointer along the digital data streams.

6. The system of claim 5 wherein the origin detection module determines the location of the intrathoracic sounds using equations of motion and geometric relationships of the microphones.

7. The system of claim 6 wherein the origin detection module further comprises a central processing unit coupled to a memory and input/output circuitry by bi-directional buses.

8. The system of claim 7 wherein the digitizing means is a digital signal processor printed circuit board connected to the input/output circuitry of the origin detection module.

9. The system of claim 6 further comprising at least one speaker connected to the signal conditioner for playing back the processed audio output of at least one microphone.

10. The system of claim 6 further comprising recording means connected to the signal conditioner for storing the processed audio output of at least one microphone.

11. The system of claim 10 wherein the recording means is a magnetic tape recorder.

12. The system of claim 6 wherein the signal conditioner comprises a preamp, an isolation device, a low pass filter, a digital gain and a high pass filter for processing the audio output of each microphone.

13. The system of claim 12 wherein each microphone has a microphone impedance and the signal conditioner has a conditioner impedance and the system further comprises a matching transformer for each microphone to match the corresponding microphone impedance with the conditioner impedance.

14. A method for localizing intrathoracic sounds within a subject, the system comprising the steps of:

placing a plurality of microphones that provide an audio output about the subject;

measuring a set of three-dimensional coordinates for each microphone;

providing the audio output from each microphone to a signal conditioner for processing to remove unwanted noise and boost signal strength;

converting the processed audio output from each microphone into a digital data stream;

synchronously pairing a master clock signal to the digital data stream for each microphone;

determining an arrival time of the intrathoracic sounds at each microphone relative to a first microphone to sense the intrathoracic sounds by reference to the master clock signal;

calculating a three dimensional point of origin of the intrathoracic sounds based upon the corresponding set of three-dimensional coordinates and arrival time for each microphone by solving equations of motion and geometric relationships of the microphones.

15. The method of claim 14 further comprising the steps of:

inputting an initial, estimated sound speed; and calculating an actual sound speed for the intrathoracic sounds.

16. The system of claim 1 further wherein the origin detection module is configured to receive an initial, estimated sound speed and to calculate an actual sound speed for the intrathoracic sounds.

17. In a system for localizing sounds emanating from within a human body in which a plurality of sensors are disposed about the body, each sensor detecting a subject sound at a different time relative to the other sensors and each having a set of three dimensional coordinates, an origin detection module comprising:

a source of arrival time differences, each arrival time difference corresponding to a given sensor and measured relative to a first sensor to detect the subject sound; and means for determining the three-dimensional location of the subject sound in response to the three dimensional coordinates and the arrival time differences corresponding to each sensor.

18. The system of claim 17 wherein the determining means further utilizes an initial sound speed and further determines the actual sound speed of the subject sound.

19. The system of claim 18 wherein the determining means is configured to define a set of spheres each disposed about a given microphone, whereby the set of spheres intersect at a point that corresponds to the location of the subject sound.

20. The system of claim 19 wherein the determining means includes a computer program configured to execute on a computer having a processor, a memory, a user interface and at least one input device, wherein the computer program defines the set of spheres and solves for the point of intersection.

* * * * *